(12) United States Patent
Dutta

(10) Patent No.: US 9,505,738 B2
(45) Date of Patent: Nov. 29, 2016

(54) FUNCTIONAL FOOD ADDITIVES

(71) Applicant: Paresh Dutta, Uppsala (SE)

(72) Inventor: Paresh Dutta, Uppsala (SE)

( * ) Notice: Subject to any disclaimer, the term of this patent is extended or adjusted under 35 U.S.C. 154(b) by 234 days.

(21) Appl. No.: 14/098,973

(22) Filed: Dec. 6, 2013

(65) Prior Publication Data

US 2014/0100267 A1     Apr. 10, 2014

Related U.S. Application Data

(63) Continuation of application No. 13/518,929, filed as application No. PCT/SE2010/051477 on Dec. 23, 2010, now Pat. No. 8,629,175.

(60) Provisional application No. 61/289,456, filed on Dec. 23, 2009.

(30) Foreign Application Priority Data

Apr. 27, 2010  (SE) ...................................... 1000426

(51) Int. Cl.
| | |
|---|---|
| *C07D 339/04* | (2006.01) |
| *A23L 1/30* | (2006.01) |
| *A23L 3/3517* | (2006.01) |
| *A23L 3/3535* | (2006.01) |
| *A23L 3/3544* | (2006.01) |
| *C07C 323/52* | (2006.01) |

(52) U.S. Cl.
CPC ............... *C07D 339/04* (2013.01); *A23L 1/30* (2013.01); *A23L 1/3006* (2013.01); *A23L 3/3517* (2013.01); *A23L 3/3535* (2013.01); *A23L 3/3544* (2013.01); *C07C 323/52* (2013.01); *A23V 2002/00* (2013.01)

(58) Field of Classification Search
None
See application file for complete search history.

(56) References Cited

U.S. PATENT DOCUMENTS 5,670,657 A    9/1997   Kojima et al.

FOREIGN PATENT DOCUMENTS

| JP | 2007-077066 | 3/2007 |
|---|---|---|
| WO | 0166560 | 9/2001 |
| WO | 2008106640 | 9/2008 |
| WO | 2009086547 | 7/2009 |

OTHER PUBLICATIONS ("What are the Health Risks of Overweight and Obesity?", https://www.nhlbi.nih.gov/health/health-topics/topics/obe/risks, accessed Mar. 7, 2016.*
Fernandez-Sanchez, International Journal of Molecular Science, Dec. 2011, 3117-32.*
International search report dated Mar. 22, 2011 in corresponding PCT/SE2010/051477.

* cited by examiner

*Primary Examiner* — Noble Jarrell
(74) *Attorney, Agent, or Firm* — Young & Thompson

(57) ABSTRACT

Novel compounds, and in particular to diacylglycerol (1, 3-DAG) and alpha-lipoic acid (LA) and/or dihydro-alpha-lipoic acid (DHLA) derivatives. In particular these novel compounds are used as functional food additives. These may for example be used as nutraceuticals and/or pharmaceuticals in the prevention and treatment of obesity, diabetes, atherosclerosis, oxidative stress and other lifestyle-related diseases.

15 Claims, 4 Drawing Sheets

1,2,3-triacyl-*sn*-glycerol (TAG)

1,3-diacyl-*sn*-glycerol (DAG)

1,2-diacyl-*sn*-glycerol (DAG)

2,3-diacyl-*sn*-glycerol (DAG)

FUNCTIONAL FOOD ADDITIVES

The present invention relates to functional food additives, and in particular to diacylglycerol (DAG) and alpha-lipoic acid (LA) and/or dihydro-alpha-lipoic acid (DHLA) derivatives. These may for example be used as nutraceuticals in the prevention and treatment of obesity, diabetes, atherosclerosis, oxidative stress and other lifestyle-related diseases.

BACKGROUND

Nutraceuticals

The term nutraceutical was introduced in the 1990's by Dr. Stephen De Feliceas: "A nutraceutical is any substance that is a food or a part of a food and provides medical or health benefits, including the prevention and treatment of disease. Such products may range from isolated nutrients, dietary supplements and specific diets to genetically engineered designer foods, herbal products, and processed foods such as cereals, soups and beverages".

Health Canada defines nutraceutical as: "a product isolated or purified from foods, and generally sold in medicinal forms not usually associated with food and demonstrated to have a physiological benefit or provide protection against chronic disease".

Diacylglycerol (DAG)

In refined edible fats and oils, triacylglycerol (TAG) content generally exceeds more than 95%. Although a minor component, the levels of DAG can be as high as ca. 10%, in some edible oils depending on the source. In humans, DAGs are produced as metabolic intermediates after ingestion of TAG, namely 1,2 (or 2,3)-diacyl-sn-glycerol (1,2-DAG). In contrast, DAG is present as 1,3-diacyl-sn-glycerol (1,3-DAG), in the cooking oils which are generated from 1,2-DAG due to heat treatment during the manufacturing process by migration of the acyl group. 1,3-DAG can also be produced by an enzymatic process with 1,3-specific lipase In addition, substantial amounts of DAG can be generated during frying of foods due to hydrolysis of TAG. Edible oil containing more than 80% DAG dominated by 1,3-DAG, commonly known as DAG oil, is commercially produced by specific lipases from edible fats and oils. Food energy content of DAG oil has been shown to be slightly lower than that of TAG oil. Chemical structures of TAG and DAG molecules are shown in FIG. 1.

DAG oil (1,3-DAG) is, in contrast to TAG, mainly utilized by the body as an energy source, rather than being stored, due to the different metabolic fates after absorption into the gastrointestinal epithelial cells. Clinical studies with animals and humans on the effects of DAG oil have shown significant decrease in body weight, thus reducing obesity-related health risks. DAG oil has been shown to be useful for patients with type 2 diabetes to prevent atherosclerotic diseases. Extensive studies have been conducted on the safety aspects of DAG consumption and no adverse effects have been reported of DAG consumption. DAG oil has been introduced in Japan in 1999 as healthy cooking oil, and in 2000, the FDA of USA stated that DAG oil was generally safe. Prepared from fats and oils, DAG is also used as emulsifiers as direct food ingredients.

α-Lipoic Acid (LA) and Dihydrolipoic Acid (DHLA)

Commercially available alpha-lipoic acid (racemic alpha-lipoic acid) is a synthetic product consisting of two forms, the R+ and S− optical isomers in equal amounts. The R+ isomer is the naturally occurring lipoic acid. This isomer (R+) is the type the body makes and requires for its efficacy. LA has been in use as a multi-tasking supplement and is popularly known as "metabolic antioxidant" or "the universal antioxidant" since it recycles vitamin C, Vitamin E and glutathione in the body. The body needs LA to produce energy in the mitochondria. In addition, LA is converted in the body into dihydrolipoic acid (DHLA), which acts as an additional antioxidant. LA is soluble both in water and fat resulting in activity both in lipid and in aqueous phase. This interesting bioactive compound has been used to treat peripheral nerve degeneration, lower cholesterol, detoxify the liver, and control blood sugar levels of the diabetics. Additionally, LA has been found to help in protecting the functionality of the mitochondria, and thus being effective against ageing.

It has been suggested that lipoic acid could be the drug of the future based on the experimental and clinical studies with drugs containing lipoic acid. It has been particularly emphasized on the antioxidant properties of LA/DHLA system for scavenging of the reactive oxygen species (ROS), chelating metal ions and regenerating cellular antioxidants. DHLA is the reduced form of LA which possesses superior antioxidant property compared with its oxidized form LA as obvious from their chemical structures. And both of these compounds have been demonstrated and suggested to be useful in treatment in a variety of pathological conditions linked to oxidative stress e.g. diabetes and cardiovascular disease, liver diseases, AIDS, age-related disorders, multiple sclerosis, Alzheimer's disease, diabetic polyneuropathy, diabetic neuropathy etc. The synergistic effect of DAG oil and phytosterols has shown higher cholesterol lowering property compared with TAG oil and phytosterols. Phytosterol lipoate and conjugates of lipoic acid with glycerol have been the subject of patent applications, namely WO 01/66560 A2; WO 2009/086547 A1; and JP 2007-077066.

SUMMARY OF THE INVENTION

The present invention relates to novel compounds usable as functional food additives. Thus, there is provided nutraceuticals selected from 1,3-diacylglycerol (DAG), alpha-lipoic acid (LA) and dihydro-alpha-lipoic acid (DHLA). These nutraceuticals may be used in treatment and prevention of obesity, diabetes, atherosclerosis, ageing, and other lifestyle-related diseases.

In one embodiment, said substances are selected from DAG-LA and/or DAG-DHLA.

Preferably, said substances are selected from the group consisting of compounds I-XII, shown in FIG. 3.

The substances according to the present invention are usable as nutraceuticals and/or pharmaceuticals.

The substances according to the present invention are also usable as antioxidants, particularly in food.

The substances according to the present invention are also usable as stabilizers, particularly in food.

The substances according to the present invention are also usable as emulsifiers, particularly in food.

The substances according to the present invention are also usable as a food additive.

The novel derivatives of the present invention, wherein LA and/or DHLA is esterified with the DAG moiety, possess advantages compared with the derivatives based on DAG alone. This is mainly due to the increased solubility and stabilizing effect against oxidative stress of the derivatives in fats and oils and in other products such as drugs. The synergistic or additive effects of DAG and LA/DHLA of the invention are contemplated to be effective in the prevention and treatment of obesity, diabetes, atherosclerosis, oxidative stress and other lifestyle-related diseases. The advantages of the present invention are described below.

The embodiments of this invention have multiple applications, where some examples are:

a) As nutraceuticals in various functional food ingredients and drugs in prevention and treatment of obesity, diabetes, atherosclerosis, oxidative stress, ageing and other lifestyle-related diseases, wherein the synergistic effect of DAG and LA and/or DHLA is utilized.

b) As stabilizers, delivering agent, and antioxidants in various functional food ingredients and drugs to extend shelf life, wherein the enhanced lipid solubility is utilized.

c) Mono-acyl-lipoates and/or mono-acyl-dilipoates and other derivatives can be used as emulsifiers in a wide range of food products (margarine products, yoghurts, ice-cream, milk based drinks etc.) for health benefits as mentioned under a and b.

The structures, synthesis and anti-oxidative activity measurement of the substances according to the present invention are shown in FIGS. 1-3, and in Table 1, respectively. The detailed description of thus are presented in examples 1-4.

DESCRIPTION OF THE INVENTION

The novel compounds are defined by the general structural formula (I)

$$\begin{array}{c} CH_2-R1 \\ | \\ CH-R2 \\ | \\ CH_2-R3 \end{array} \quad (I)$$

wherein
at least one, but not more than two of R1, R2 and R3, is/are L-COO—, wherein L is either

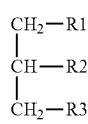

(2)

or

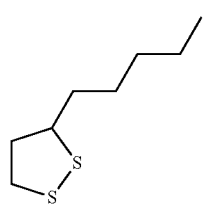

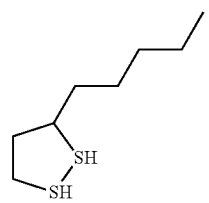

(3)

or both if there is more than one L in the structure and wherein the other of R1, R2 and R3 is selected from the group consisting of —OH and any naturally occurring fatty acids according to the formula R—COOH, wherein R is an alkyl or an alkenyl, and wherein the hydrocarbon chain is straight or branched.

The carbon chain R suitably contains at least 3, but as many as 21 carbon atoms, although any number of carbons there between is possible, such as 5, 6, 7, 8, 9, 10, 11, 12, 13, 14, 15, 16, 17, 18, 19 or 20. In case of alkenyl it contains up to 6 double bonds, i.e. at least one double bond, but alternatively 2, 3, 4, 5 or 6 double bonds.

Suitably, L is always the same if there is more than one L in the structure.

Below a number of possible structures for compounds according to the present invention is shown.

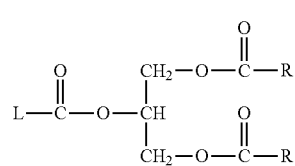

I

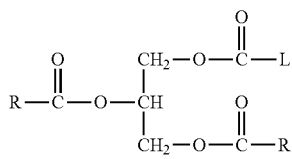

II

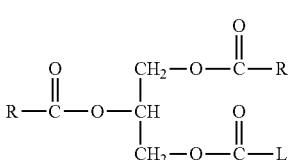

III

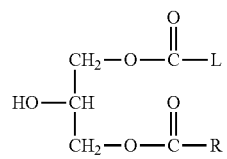

IV

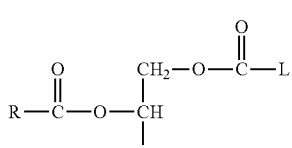

V

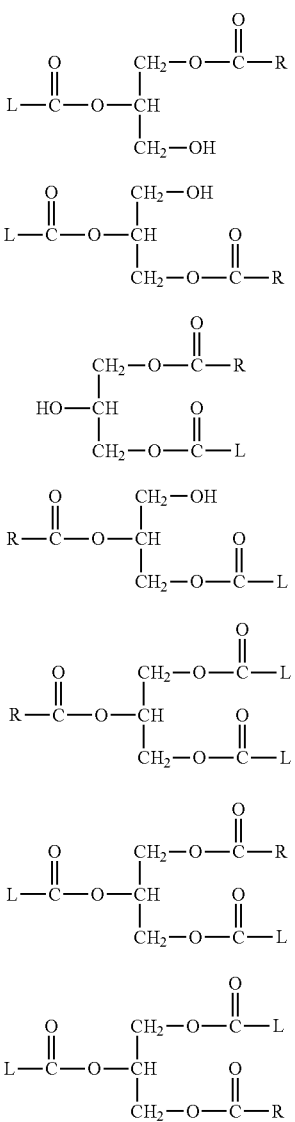

In the formulae I-XII above L can be any of the structures according to formula (2) or (3) above and R can be an alkyl or an alkenyl hydrocarbon chain (straight or branched up to 21 carbon atoms) without or with up to six double bonds as defined above in formula (1)

Benefit and Potential Applications of DAG-LA and/or DAG-DHLA

Figure 1:
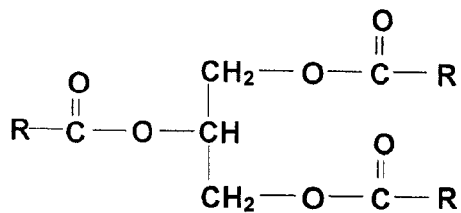
FIG. 1 shows examples of previously known TAG and DAG derivatives.
Figure 1:
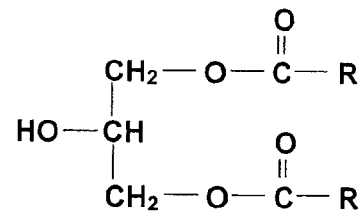
Figure 1:
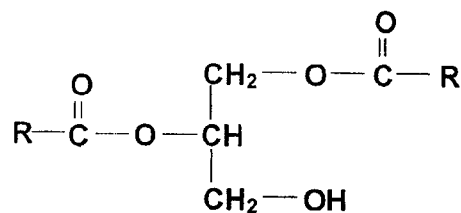
Figure 1:
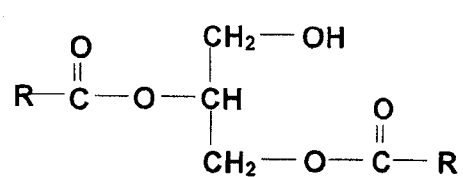
Figure 2:
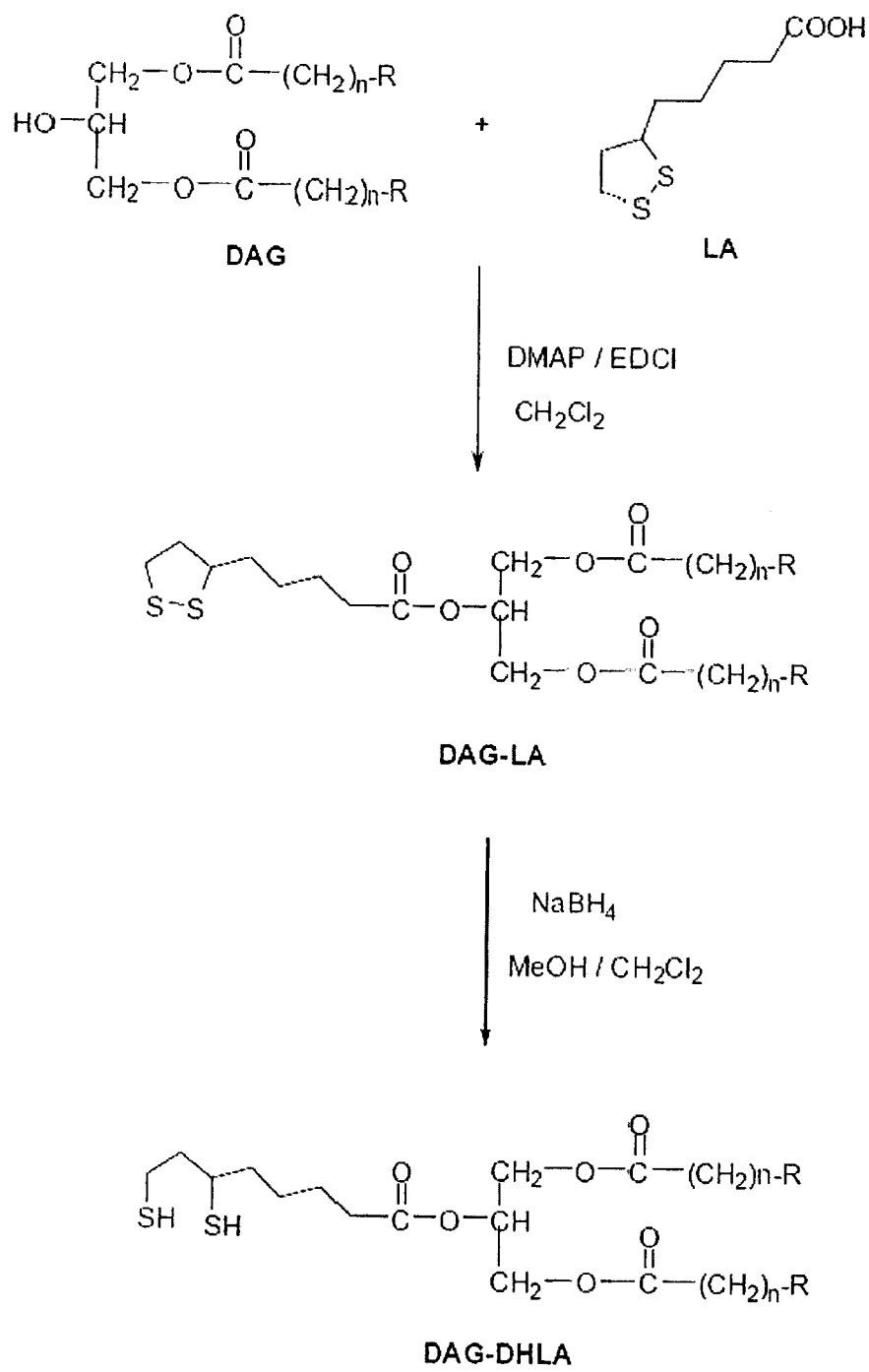
FIG. 2 shows a synthesis scheme for making DAG-LA and DAG-DHLA according to the present invention.

The present invention relates to new chemical structures or compounds wherein a DAG moiety is chemically esterified with LA and/or DHLA (compounds I-XII, FIG. 2 are examples of compounds according to the invention). This derivatisation would benefit and enhance the structural entities of the new structure. The esters of the LA and/or DHLA moiety with DAG are readily soluble in fats and oils or in any lipid media. Thus, it would be possible to utilize these derivatives in more versatile applications, e.g. not only in fats and oils for food preparations but also as potential stabilizer of health beneficial polyunsaturated fatty acid preparations, and other products such as drugs. The potential synergistic and or additive effect between DAG and LA and/or DHLA is contemplated to be used for health benefits and prevention of obesity, diabetes, cardiovascular diseases, oxidative stress and inflammation, ageing, cancer, Alzheimer's, and against lifestyle-related diseases such as obesity, heart disease, hypertension, type 2-diabetes, colon cancer, and premature mortality. The derivatives contemplated to facilitate utilization of LA without being decomposed and stable to oxidation at elevated temperatures and during food processing, handling and storage conditions.

EXAMPLES

The present invention is described by the following non-limiting examples:
General Procedure and Materials
Abbreviation List:
DAG Diacyl-sn-glycerol
LA Lipoic acid
DHLA Dihydrolipoic acid
DAG-LA Diacyl-lipoyl-sn-glycerol
DAG-DHLA Diacyl-dihydrolipoyl-sn-glycerol
DMAP 4-Dimethylaminopyridine
EDCI 1-Ethyl-3-(3-dimethylaminopropyl) carbodiimide hydrochloride
PMA Phosphomolybdic acid
Brine Aqueous saturated sodium chloride
TLC Thin-layer-chromatography
NMR Nuclear magnetic resonance
TMS Tetramethylsilane 1,3-Dioleinyl-sn-glycerol from Nu-Check Prep, Inc., (Elysian, Minn., USA) and lipoic acid were purchased from Sigma-Aldrich AB (Stockholm, Sweden). Chemicals and solvents unless otherwise specified in the syntheses of the compounds in the examples, were commercially available from WVR International AB (Stockholm, Sweden). Chromatographic separations were performed using silica gel (60 Å, 200-400 mesh). The compounds were analyzed by TLC: silica plates (Merck 60); compounds were visualized by treatment with a 10% solution of PMA in ethanol followed by heating. $^{1}$H and $^{13}$C NMR spectra were conducted on a Bruker 400 MHz spectrometer and chemical shifts ($\delta$) are given in ppm relative to TMS. The spectra were recorded in CDCl$_3$ as solvent at room temperature.

Example 1

Preparation of DAG-LA

The synthesis of DAG-LA was performed following a published method with some modifications (Chiu, C. C. et al. (1996). *J. Am. Chem. Soc.* 118:11026-11029). To a solution of DAG (1.61 mmol) in CH$_2$Cl$_2$ (9 mL) was added DMAP (42 mg, 0.34 mmol), LA (435 mg, 2.11 mmol) and EDCI (310 mg, 1.62 mmol) at 0° C. with stirring. The reaction mixture stirred at room temperature overnight. Extractive workup (CH$_2$Cl$_2$, dilute HCl, water, brine), drying (Na$_2$SO$_4$) of the combined organic extracts and concentration furnished the crude which was purified by chromatography to give the pure compound:

1,3-Dioleoyl-2-lipoyl-sn-glycerol (1)

Figure 3:
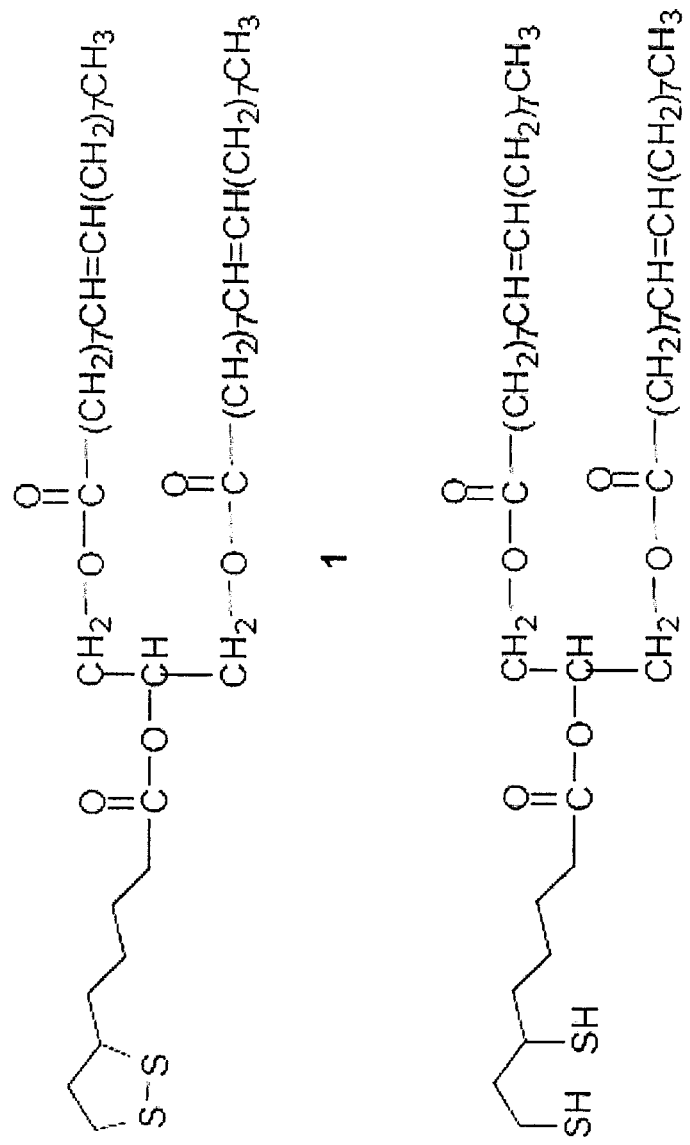
FIG. 3 shows the structures of 1, 3-dioleoyl-2-lipoyl-sn-glycerol (1), and 1,3-dioleoyl-2-dihydrolipoyl-sn-glycerol (2)

Structure Shown in FIG. 3

(1 g, 80%). $^{1}$H NMR (CDCl$_3$, 400 MHz), ($\delta$) 5.45-5.30 (m, 4H), 5.28-5.20 (m, 1H), 4.35-4.25 (m, 2H), 4.18-4.10 (m, 2H), 3.60-3.50 (m, 1H), 3.21-3.06 (m, 2H), 2.50-2.40 (m, 1H), 2.35-2.28 (m, 6H), 2.05-1.96 (m, 8H), 1.95-1.85

(m, 1H), 1.75-1.56 (m, 8H), 1.55-1.40 (m, 2H), 1.39-1.20 (m, 40H), 0.92-0.85 (m, 6H). $^{13}$C NMR (CDCl$_3$, 100 MHz), (δ) 173.2, 172.5, 130.0, 129.7, 69.1, 62.0, 56.3, 40.2, 38.5, 34.6, 34.0, 33.9, 31.9, 29.8, 29.7, 29.5, 29.4, 29.3, 29.2, 29.1, 29.0, 28.7, 27.3, 27.2, 24.8, 24.6, 22.7, 14.1.

Example 2

Preparation of DAG-DHLA

The synthesis of DAG-DHLA was conducted following a published method with some modifications (Chittiboyina et al. (2006). *J. Med. Chem.* 49:4072-4084). DAG-LA (0.247 mmol) was dissolved in CH$_2$Cl$_2$/MeOH (1:5, 12 mL) under N$_2$. NaBH$_4$ (14 mg, 0.371 mmol) was added in portions and the reaction mixture stirred at room temperature under N$_2$. After about 2 h, aqueous 1M HCl (5 mL) was added. Extractive workup (CH$_2$Cl$_2$, dilute HCl, water, brine), drying (Na$_2$SO$_4$) of the combined organic extracts and concentration furnished the crude which was purified by chromatography to give the pure compound:

1,3-Dioleoyl-2-dihydrolipoate-sn-glycerol (2)

(140 mg, 70%). $^1$H NMR (CDCl$_3$, 400 MHz), (δ) 5.43-5.35 (m, 4H), 5.30-5.25 (m, 1H), 4.36-4.25 (m, 2H), 4.20-4.12 (m, 2H), 3.01-2.90 (m, 1H), 2.80-2.65 (m, 2H), 2.40-2.30 (m, 6H), 2.10-1.86 (m, 9H), 1.80-1.45 (m, 11H), 1.40-1.20 (m, 42H), 0.95-0.86 (m, 6H). $^{13}$C NMR (CDCl$_3$, 100 MHz), (δ) 173.2, 172.5, 130.0, 129.7, 69.1, 62.0, 42.8, 39.3, 38.7, 34.2, 34.0, 31.9, 29.8, 29.7, 29.6, 29.5, 29.4, 29.3, 29.2, 29.1, 27.2, 27.1, 26.6, 24.8, 24.5, 22.7, 22.3, 14.1.

Example 3

Antioxidant Activity of DAG-DHLA

The antioxidant (AO) activity of DAG-DHLA was determined using DPPH$^•$ radical following the published methods (Brand-Williams, W. et al. (1995). *Lebensm. Wiss. U.-Technol.* 28:25-30).

Antioxidant solution in toluene (0.1 mL) was added to 3.9 mL of a 6×10$^{-5}$ mol/L toluene DPPH$^•$ solution. Absorbance was determined at 515 nm at 0 min, and every 30 min until the reaction 'reached a plateau. For each DAG-DHLA concentration tested, the reaction kinetics was plotted. From this graph, the percentage of DPPH$^•$ remaining at the steady state was recorded and the values transferred onto another graph showing the percentage of residual DPPH$^•$ at the steady state as a function of the molar ratio of antioxidant to DPPH$^•$ Experiment with DAG-LA was conducted in parallel but showed negligible antioxidant activity compared with DAG-DHLA. Antiradical activity was defined as the amount of antioxidant necessary to decrease the initial DPPH$^•$ concentration by 50% (Efficient Concentration=EC50 ((mol/L) AO/(mol/L) DPPH$^•$). From this EC50 value, antiradical power (APR) value was calculated from 1/EC50, the larger the ARP, the more efficient the antioxidant and the results are shown in Table 1 which shows EC50 value of 1,3-Diolyol-2-dihydrolipoyl-sn-glycerol (DAG-DHLA), based on the disappearance of DPPH$^•$ as a function of number of moles of DAG-dihydrolipoate/mole DPPH$^•$:

TABLE 1

Antiradical efficiency and stoichiometry of 1,3-dioleoyl-2-dihydrolipoyl-sn-glycerol (2) (structure shown in FIG. 3)

| Kinetic behaviour | EC$_{50}$ | ARP | Stoichiometric value | Number of reduced DPPH$^•$ |
|---|---|---|---|---|
| Rapid | 0.21 | 4.68 | 0.43 | 2.34 |

EC$_{50}$ (Efficient concentration) = the amount of antioxidant 2 necessary to decrease the initial DPPH$^•$ concentration by 50%
ARP = Antiradical power = 1/EC$_{50}$
Stoichiometric value = EC$_{100}$ = 2 × EC$_{50}$
Number of reduced DPPH$^•$ (1/EC$_{100}$) = the number of DPPH$^•$ moles reduced by one mole of antioxidant 2.

Example 4

Animal Study with DAG-LA and DAG-DHLA Conjugates

Figure 4:
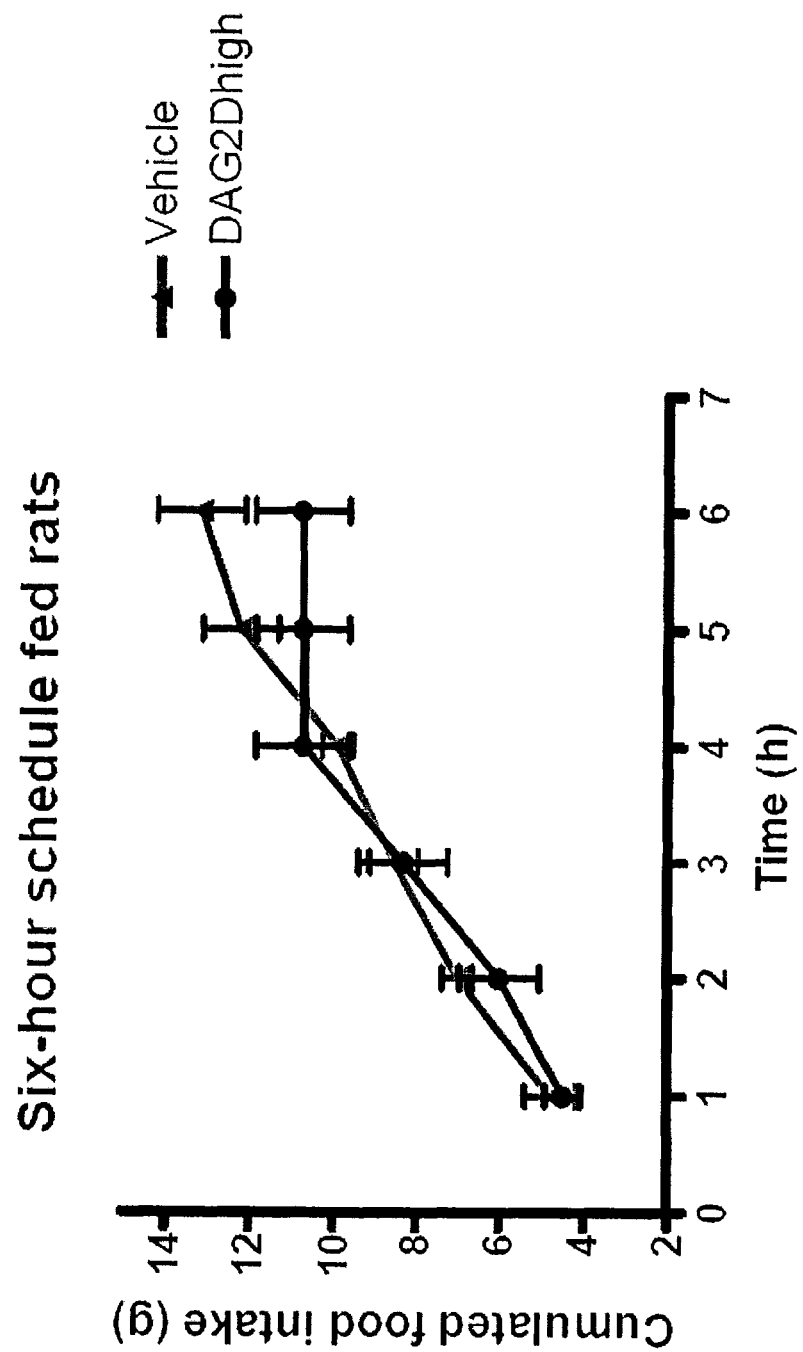
FIG. 4 shows effects of DAG2D on acute food intake in rats.

An acute experiment with rats has been conducted recently after complying with Swedish Ethical regulations. Seven groups of rats (n=4-5) were given an acute test dose (100-200 mg/kg) of the control vehicle (rapeseed oil) and test conjugates. Part of the results is shown here in FIG. 4. As can be seen from FIG. 4, the DAG-DHLA (DAG2D, 200 mg/kg) conjugate seems to block food intake after 4 hours compared to vehicle. Rather similar result was also observed with DAG-LA conjugate.

The mechanism of anti-obesity effects of DAG is not clearly understood and several pathways are suggested. After consumption, 1,3-DAG are converted into 1- (or 3-) monoacylglycerols by the 1,3-lipases in the small intestine, similar to the absorption of TAG in the body. This 1,3-DAG is able to increase β-oxidation, to enhance body weight loss, to suppress body fat accumulation and to lower postprandial serum TAG levels. Further, DAGs are suggested to decrease the resynthesis of chylomicrons as well as shunting them directly to the liver through the portal vein, where they are oxidized. Thus the increased fat oxidation may influence food intake by increasing satiety and subsequently reduce body weight.

Recent studies with LA acid supplementation has shown considerable body weight reduction in obese animals by reducing food intake and enhancing energy expenditure and has been suggested to be an ideal candidate for treatment of obesity and related diseases. The results from the acute experiment may be due to synergistic effect of DAG and LA.

Therefore it is within the inventive concept to treat or prevent a disease or disease condition in a subject in need thereof, comprising providing a composition comprising a novel molecule as defined herein and administering a therapeutically effective amount of the composition to the subject. In particular, the disease or disease condition is selected from the group consisting of obesity, diabetes, atherosclerosis, oxidative stress and other lifestyle-related diseases.

The invention claimed is:
1. A compound defined by the structural formula

wherein at least one, but not more than two of R1, R2 and R3, is/are L-COO—, wherein L is either

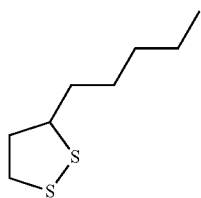
(2)

or

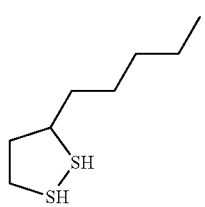
(3)

or both if there is more than one L in the structure and wherein the other of R1, R2 and R3 is selected from the group consisting of —OH and fatty acids according to the formula R—COOH, wherein R is an alkyl or an alkenyl with 1-6 double bonds, and wherein the hydrocarbon chain is straight and has a length of 3 or more carbon atoms but 21 or less carbon atoms, with the proviso that only one of R1, R2 and R3 is —OH.

2. The compound according to claim 1, wherein the hydrocarbon chain has a length of 5 or more carbon atoms but with 21 carbon atoms or less.

3. The compound according to claim 1, wherein L is always the same if there is more than one L in the structure.

4. A food additive comprising the compound according to claim 3.

5. A nutraceutical comprising the compound according to claim 1.

6. An anti-oxidant comprising the compound according to claim 1.

7. An emulsifier for food comprising the compound according to claim 1.

8. A stabilizer for food and pharmaceuticals comprising the compound according to claim 1.

9. An agent for blocking food intake comprising the compound according to claim 1.

10. The compound according to claim 1, wherein the structural formula is selected from the group consisting of:

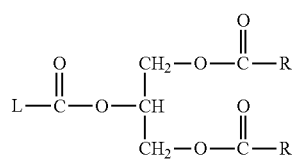
I

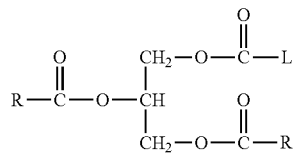
II

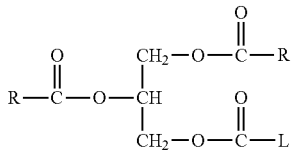
III

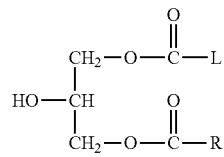
IV

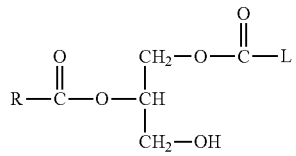
V

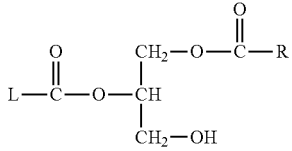
VI

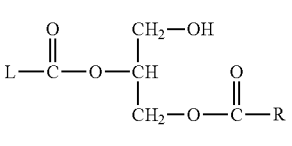
VII

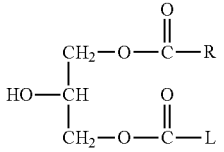
VIII

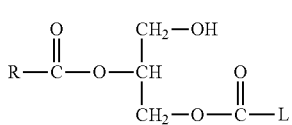
IX

-continued

X

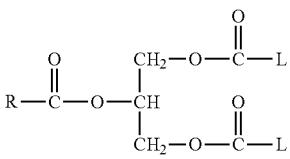

XI

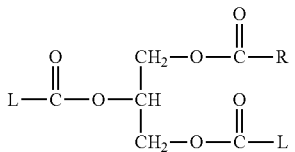

XII

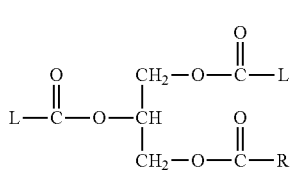

wherein
L is according to formula (2) or formula (3)

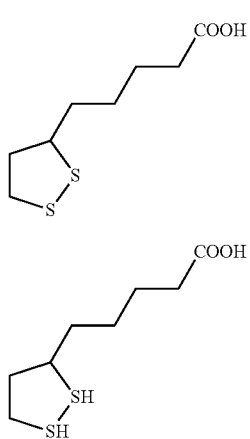

or both if there is more than one L in the structure, and wherein R is an alkyl or an alkenyl with 1-6 double bonds, and wherein the hydrocarbon chain is straight and has a length of 3 or more carbon atoms but 21 or less carbon atoms.

11. A method of treating or inhibiting obesity and/or a disease or disease condition depending on an obesity status selected from the group consisting of diabetes, atherosclerosis, oxidative stress, in a subject in need thereof, comprising administering a therapeutically effective amount of the compound according to claim 1 to the subject.

12. A compound defined by the structural formula

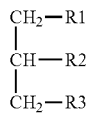

wherein R2 is

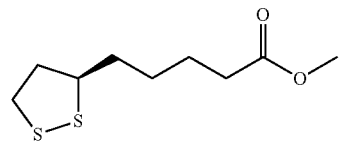

and wherein R1 and R3 are selected from the group consisting of —OH and fatty acids according to the formula R—COOH, wherein R is an alkyl or an alkenyl with 1-6 double bonds, and wherein the hydrocarbon chain is straight and has a length of 3 or more carbon atoms but 21 or less carbon atoms, with the proviso that only one of R1 and R3 is —OH.

13. A compound defined by the structural formula:

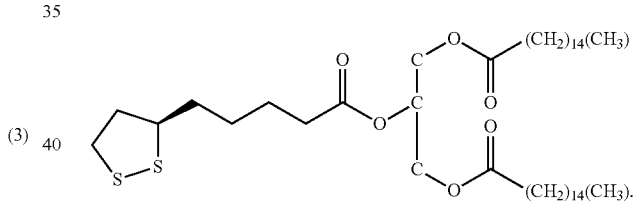

14. A compound defined by the structural formula:

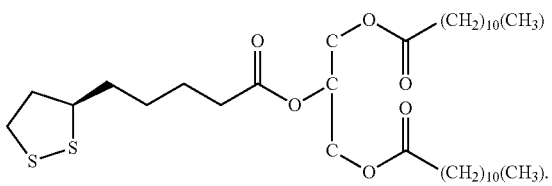

15. A compound defined by the structural formula:

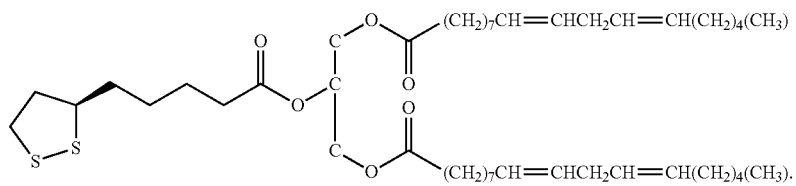

* * * * *